Figure 1:
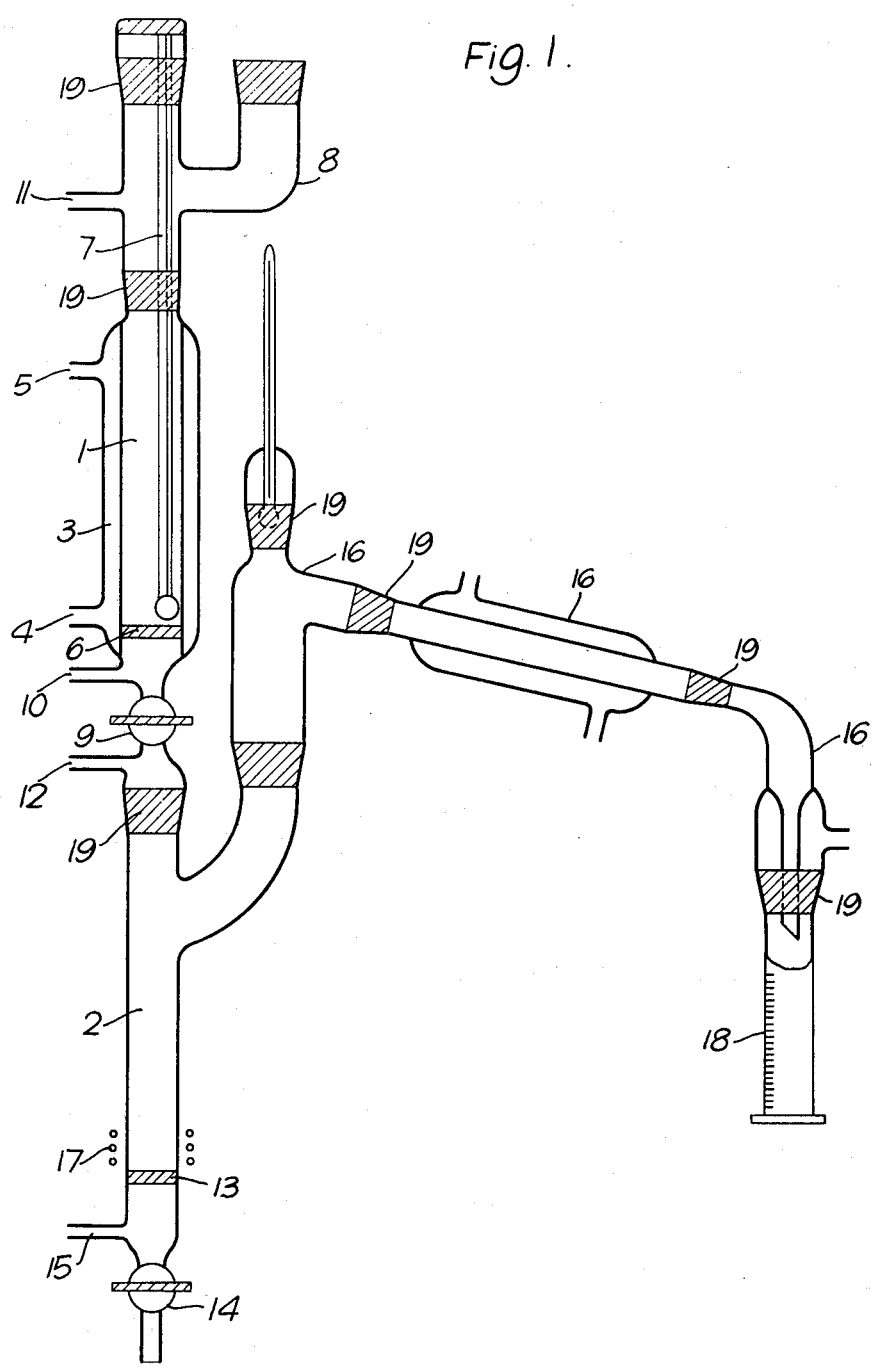

United States Patent [19]

Horner et al.

[11] 4,016,210
[45] Apr. 5, 1977

[54] CRYSTALLIZATION PROCESS

[75] Inventors: Patrick James Horner, Welwyn Garden City, England; John Peter Brown, Westport, Conn.

[73] Assignee: Imperial Chemical Industries Limited, London, England

[22] Filed: Oct. 23, 1975

[21] Appl. No.: 625,124

Related U.S. Application Data

[63] Continuation-in-part of Ser. No. 566,511, April 8, 1975, abandoned.

[30] Foreign Application Priority Data

Apr. 16, 1974 United Kingdom ............ 16448/74
Apr. 16, 1974 United Kingdom ............ 16444/74

[52] U.S. Cl. .................... 260/607 AR; 260/543 H
[51] Int. Cl.² ........................................ C07C 147/08
[58] Field of Search ............................ 260/607 AR

[56] References Cited

UNITED STATES PATENTS

| | | | |
|---|---|---|---|
| 2,556,429 | 6/1951 | Lee | 260/607 AR |
| 2,593,001 | 4/1952 | Bender et al. | 260/607 AR |
| 3,297,766 | 1/1967 | Bradley et al. | 260/607 AR |
| 3,383,421 | 5/1968 | Fox et al. | 260/607 AR |
| 3,579,590 | 5/1971 | Davis | 260/607 AR |
| 3,632,642 | 1/1972 | Rosin et al. | 260/607 AR |
| 3,855,312 | 12/1974 | Horner | 260/607 AR |

*Primary Examiner*—Lewis Gotts
*Assistant Examiner*—D. R. Phillips
*Attorney, Agent, or Firm*—Cushman, Darby & Cushman

[57] ABSTRACT

A process is provided for the crystallization of bis-(4-chlorophenyl) sulphone from a reaction mixture in which it is formed by reacting chlorobenzene sulphonic acid and chlorobenzene which comprises (i) forming a crystallization liquor from the reaction mixture by adjusting the weight ratio of chlorobenzene to chlorobenzene sulphonic acid of the reaction mixture so as to maximize the quantity of bis-(4-chlorophenyl) sulphone which can crystallize from the liquor at a desired crystallization temperature, and (ii) allowing the bis-(4-chlorophenyl) sulphone to crystallize from the crystallization liquor at the temperature.

8 Claims, 4 Drawing Figures

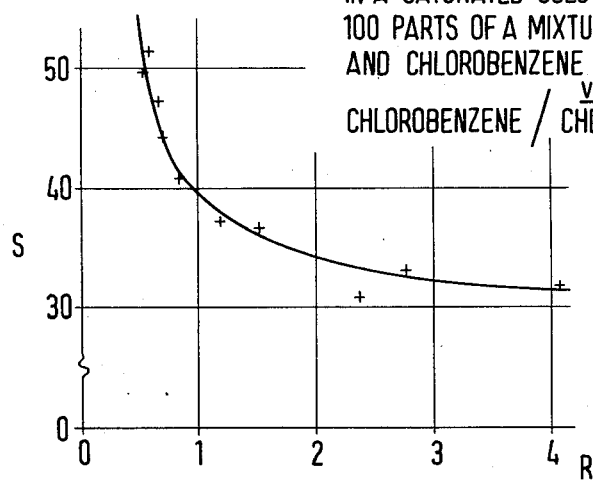

Fig. 2. AMOUNT OF BIS (CHLOROPHENYL) SULPHONE (S) IN A SATURATED SOLUTION AT 18°C. PER 100 PARTS OF A MIXTURE OF CHLOROBENZENE AND CHLOROBENZENE SULPHONIC ACID

CHLOROBENZENE / CHLOROBENZENE SULPHONIC ACID RATIO (R).

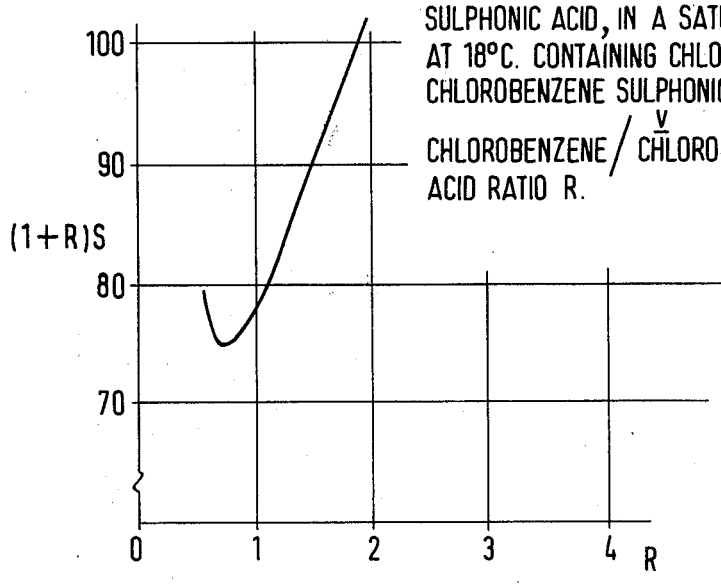

Fig. 3. AMOUNT OF BIS (CHLOROPHENYL) SULPHONE (S), PER 100 PARTS OF CHLOROBENZENE SULPHONIC ACID, IN A SATURATED SOLUTION, AT 18°C. CONTAINING CHLOROBENZENE AND CHLOROBENZENE SULPHONIC ACID I.E. (1+R)S

CHLOROBENZENE / CHLOROBENZENE SULPHONIC ACID RATIO R.

CRYSTALLIZATION PROCESS

This is a continuation-in-part application of our application Ser. No. 566,511 filed Apr. 8, 1975 and now abandoned.

This invention relates to crystallisation of bis-(4-chlorophenyl) sulphone from a reaction mixture in which it is formed.

Bis-(4-chlorophenyl) sulphone is an important monomer for the preparation of aromatic polymers as described for example in British patent specification Nos. 1,078,234 and 1,153,035 and U.S. Pat. specification Nos. 3,432,468. In the patent specifications, bis-(4-chlorophenyl) sulphone is reacted with alkali metal hydroxides, hydrosulphides or sulphides or the di-alkali metal salts of dihydric phenols and thiophenols. Bis-(4-chlorophenyl) sulphone can also be used for the production of bis-(4-aminophenyl) sulphone in the pharmaceutical industry. for these applications bis-(4-chlorophenyl) sulphone is required in a high state of purity, substantially free of sulphonic acids and isomeric sulphones, particularly 3,4'- and 2,4'-dichlorodiphenyl sulphone.

Bis-(4-chlorophenyl) sulphone can be made by the reaction of chlorobenzene sulphonic acid, preferably the 4-isomer, and chlorobenzene. The chlorobenzene sulphonic acid can be prepared in situ by reacting chlorobenzene with for example, sulphuric acid or sulphur trioxide. The reactions may be carried out in a sealed vessel, or at elevated temperature under atmospheric or superatmospheric pressure. In order for yields of bis-(chlorophenyl) sulphones to be maximised, water formed during the condensation reaction must be removed as efficiently as possible. However the reaction conditions must be carefully controlled so as to maximise the yield of bis-(4-chlorophenyl) sulphone whilst minimising the yields of other isomers and dark coloured reaction by-products, otherwise extraction of bis-(4-chlorophenyl) sulphone may be difficult and commercially unattractive.

A particularly preferred process for the production of bis-(4-chlorophenyl) sulphone is described in U.S. Pat. No. 3,855,312 wherein a reaction mixture containing 4-chlorobenzenesulphonic acid and chlorobenzene is kept at a temperature lying between 220° C and 260° C at a superatmospheric pressure lying between 4 and 160 p.s.i. (30 and 1100 kN/m²), water is removed as vapour continuously as it is formed, and the water vapour and accompanying chlorobenzene vapour are condensed and separated and the chlorobenzene is returned to the reaction mixture. Desirably, the 4-chlorobenzene sulphonic acid is formed in situ.

In such a process the product is a mixture of bis-(4-chlorophenyl) sulphone, isomers, such as the 2,4'- and 3,4'-isomers, chlorobenzene and chlorobenzene sulphonic acid. This mixture is hereinafter termed the reaction product. At elevated temperatures e.g. above about 90° C, this mixture is in the form of a solution of the bis(4-chlorophenyl) sulphone and isomers dissolved in a mixture of chlorobenzene and chlorobenzene sulphonic acid.

It is then necessary to separate the bis(4-chlorophenyl) sulphone from the reaction product. Heretofore the normal way of separating bis(4-chlorophenyl) sulphone from the reaction medium in which it is produced is by admixing the reaction medium with water whereupon the bis(4-chlorophenyl) sulphone precipitates, together with the undesired isomers.

We have found that, surprisingly, bis(4-chlorophenyl) sulphone can be isolated from the reaction product in good purity simply by crystallisation of the reaction product.

Thus separation of the bis(4-chlorophenyl) sulphone may be effected by crystallisation by cooling the reaction product from a temperature at which the sulphones are dissolved down to a suitable temperature and at which the bis(4-chlorophenyl) sulphone crystallises and then separating the crystallised bis-(4-chlorophenyl) sulphone. This temperature is herein referred to as the crystallisation temperature although it will be appreciated that crystallisation will occur as the reaction product is cooled down to this temperature.

It is however desirable to obtain as large an amount of the bis-(4-chlorophenyl) sulphone from the reaction product as is economically viable. At any given crystallisation temperature, the maximum amount of bis-(4-chlorophenyl) sulphone that can be recovered by crystallisation is determined by the solubility of the bis-(4-chlorophenyl) sulphone in the solvents at that temperature and the quantities of the solvents present.

We have found that the maximum amount of bis-(4-chlorophenyl) sulphone that can be recovered is dependant on the proportion of chlorobenzene to chlorobenzene sulphonic acid in the liquid from which the bis-(4-chlorophenyl) sulphone is crystallised.

By adjusting the ratio of chlorobenzene to chlorobenzene sulphonic acid of the reaction product to form a crystallisation liquor, i.e. a solution from which bis-(4-chlorophenyl) sulphone will crystallise upon cooling to the crystallisation temperature, we have found that it is possible to maximise the amount of bis-(4-chlorophenyl) sulphone recovered.

This in some cases chlorobenzene can be added to the reaction product and, in spite of the increased mass of the solution, more bis-(4-chlorophenyl) sulphone can be recovered. In other cases it may be necessary to remove some chlorobenzene from the reaction product to maximise the recovery. It will of course be appreciated that the mass of the reaction product should not be reduced to too great an extent by removal of chlorobenzene as then there may be a loss of yield because of the higher solubility of bis-(4-chlorophenyl) sulphone in chlorobenzene sulphonic acid.

If the initial composition of a reaction product is: bis(4-chlorophenyl) sulphone $X\%$, chlorobenzene $y\%$; and chlorobenzene sulphonic acid $z\%$ (by weight), the ratio $(R)$ of chlorobenzene to chlorobenzene sulphonic acid is $y/z$ and the total amount of solvent (i.e. chlorobenzene plus chlorobenzene sulphonic acid) per 100 parts by weight of reaction product is $y+z$ parts, which equals $z(1+R)$ parts. This will also be the amount of solvent in the mother liquor remaining after crystallisation of the bis(4-chlorophenyl) sulphone from 100 parts by weight of the reaction product. Let the amount of bis(4-chlorophenyl) sulphone dissolved in a saturated solution containing 100 parts by weight of a mixture of chlorobenzene and chlorobenzene sulphonic acid of chlorobenzene/chlorobenzene sulphonic acid ratio $(R)$ at the crystallisation temperature be $S$ parts. Then the amount of bis(4-chlorophenyl) sulphone dissolved in the mother liquor remaining after crystallisation of 100 parts of the reaction product equals $$S \times \frac{z(1+R)}{100}$$

parts.

The amount of bis(4-chlorophenyl) sulphone recovered by crystallisation, per 100 parts by weight of reaction product, is then $$X - \left( S \times \frac{z(1+R)}{100} \right)$$

parts. In order to maximise this amount, the amount of chlorobenzene present is modified.

Thus suppose, to 100 parts by weight of the above reaction product, we add $\Delta y$ parts of chlorobenzene. The ratio ($R_1$) of chlorobenzene to chlorobenzene sulphonic acid of the modified reaction product is therefore $$\frac{y + \Delta y}{z}$$

and the total amount of solvent in the modified reaction product, and hence in the mother liquor resulting from crystallisation of the reaction product, per 100 parts of original reaction product, is $$y + \Delta y + z$$

which equals $$z(1 + R_1)$$

If the amount of bis(4-chlorophenyl) sulphone dissolved in that mother liquor, per 100 parts of solvent is $S_1$, then the amount of bis(4-chlorophenyl) sulphone dissolved per $$z(1 + R_1)$$

parts of solvent is $$S_1 \times \frac{z(1 + R_1)}{100}$$

parts and so the amount of bis(4-chlorophenyl) sulphone recovered by crystallisation is $$X - \left( S_1 \times \frac{z(1 + R_1)}{100} \right)$$

parts.

The amount recovered will thus be a maximum, for any given reaction product and crystallisation temperature, when the function $S(1 + R_1)$ is at a minimum.

The solubility of bis(4-chlorophenyl) sulphone in a mixture of chlorobenzene and chlorobenzene sulphonic acid may be determined by the following technique using the apparatus illustrated in accompanying FIG. 1.

The apparatus illustrated in FIG. 1 is fabricated from glass and comprises an upper vessel 1 and lower vessel 2. The upper vessel 1 is provided with a water jacket 3 having inlet 4 and outlet 5, and a sintered glass disc 6. The upper vessel is also provided with a thermometer 7, condenser outlet 8 and an outlet tap 9 and nitrogen pressure couplings 10 and 11 for the upper vessel and coupling 12 for the lower vessel 2. The lower vessel 2 is provided with sintered glass disc 13, outlet tap 14, nitrogen coupling 15 and distillation apparatus 16. The lower vessel is also provided with electrical cuff heater 17. Distillate is collected in measuring cylinder 18. Component parts of the apparatus are inter connected using ground glass cone-socket joints 19.

In order to measure the solubility of bis-(4-chlorophenyl) sulphone in chlorobenzene containing chlorobenzene sulphonic acid, an excess of pure recrystallised bis-(4-chlorophenyl) sulphone is placed on sintered glass disc 6 and a known weight of liquor containing known amounts of chlorobenzene and chlorobenzene sulphonic acid and optionally bis-(4-chlorophenyl) sulphone is placed in upper vessel 1. A nitrogen purge from coupling 10 to 11 is continually provided to ensure that no liquor passes below sintered glass disc 6. Water at the required constant temperature is fed through jacket 3 and the system allowed to equilibrate for about 3 hours and thus form a saturated solution.

An amount of water is placed in vessel 2 and nitrogen purge provided from coupling 15 to 12. Outlet tap 9 is opened, nitrogen purge altered to flow from 11 to 10, and the saturated solution allowed to pass from vessel 1 to vessel 2. The bis-(4-chlorophenyl) sulphone in the saturated solution is thus precipitated by the water on to sintered glass disc 13. Tap 9 is then closed. Chlorobenzene and water are then distilled azeotropically from vessel 2 using heater 17 and distillation continued until no further chlorobenzene is collected in cylinder 18. The chlorobenzene and water separate into layers in cylinder 18 and the amount of chlorobenzene is measured.

The aqueous liquor remaining in vessel 2 is discharged through tap 14 and differentially analysed to determine the content of chlorobenzene sulphonic acid and sulphuric acid (if any).

The apparatus is carefully dried and the weight of bis(4-chlorophenyl) sulphone on sintered glass disc 13 is measured.

By the above technique the solubility of bis(4-chlorophenyl) sulphone in mixtures of chlorobenzene and chlorobenzene sulphonic acid at 18° C was measured. The solution had the compositions shown in the table below.

From the data of the composition of the saturated solution, the amount of bis(4-chlorophenyl) sulphone (S) dissolved in 100 parts by weight of the solvent mixture can be calculated. This is also listed in the table.

| Ratio of chlorobenzene to chlorobenzene sulphonic acid (R) | Composition of saturated solution % by weight | | | Amount of bis(4-chlorophenyl) sulphone dissolved per 100 parts of mixture of chlorobenzene and chlorobenzene sulphonic acid (S) |
| --- | --- | --- | --- | --- |
| | bis(4-chlorophenyl) sulphone | chlorobenzene | chlorobenzene sulphonic acid | |
| 0.53 | 33.24 | 22.99 | 43.77 | 49.79 |
| 0.58 | 33.91 | 24.13 | 41.96 | 51.30 |
| 0.66 | 32.10 | 26.95 | 40.95 | 47.27 |
| 0.69 | 30.58 | 28.24 | 41.18 | 44.05 |
| 0.84 | 29.06 | 33.54 | 37.41 | 40.96 |
| 1.18 | 27.14 | 39.57 | 33.29 | 37.25 |
| 1.51 | 26.9 | 43.98 | 29.12 | 36.80 |
| 2.37 | 23.61 | 53.61 | 22.64 | 30.96 |
| 2.76 | 24.92 | 55.15 | 19.93 | 33.19 |
| 4.03 | 24.08 | 60.84 | 15.08 | 31.72 |

Similarly the compositions of saturated solutions at other temperatures can be determined.

A graph showing the variation of S with R at a crystallisation temperature of 18° C is shown in FIG. 2.

From this it is also possible to plot the function $S(1 + R)$ against R - this graph is shown in FIG. 3.

It is seen that, as the proportion of chlorobenzene increases, the amount dissolved, per 100 g of the reaction product, first decreases, since chlorobenzene is a poorer solvent than chlorobenzene sulphonic acid for bis-(4-chlorophenyl) sulphone, and then increases. The increase is because the increased mass of the solution (due to the addition of chlorobenzene) can dissolve more bis-(4-chlorophenyl) sulphone is spite of its lower solubility in chlorobenzene. The curve thus passes through a minimum. It is seen that the minimum occurs when R is about 0.74 and $S(1 + R)$ is about 74.6.

Hence the maximum amount of bis(4-chlorophenyl) sulphone recoverable at a crystallisation temperature of 18° C is $$X - 0.746\ z$$

i.e. percentage bis(4-chlorophenyl) sulphone (of reaction product) $- 0.746\ x$ percentage chlorobenzene sulphonic acid (of reaction product). The chlorobenzene/chlorobenzene sulphonic acid ratio, R, at the minimum may vary for different crystallisation temperatures and also the amount of bis-(4-chlorophenyl) sulphone dissolved, per 100 g of the reaction product, will vary with crystallisation temperature.

It will be appreciated that while it is generally desirable to perform the crystallisation with a chlorobenzene/chlorobenzene sulphonic acid ratio at near that which gives the minimum amount dissolved, this is not essential. Indeed it may be necessary for other reasons to use a ratio other than that which gives the minimum. However the chlorobenzene/chlorobenzene sulphonic acid ratio should be such that the amount of bis-(4-chlorophenyl) sulphone dissolved is no more than 5 g, per 100 g of the reaction product, above the minimum obtainable. If the amount dissolved in the saturated solution is more than this amount above the minimum, the process becomes less economical.

In this specification, the saturated solution obtained by cooling a crystallisation liquor to the crystallisation temperature and separating the crystallised bis-(4-chlorophenyl) sulphone therefrom' is termed the mother liquor.

Accordingly we provide a process for the separation of bis-(4-chlorophenyl) sulphone from a reaction product obtained by reacting chlorobenzene sulphonic acid and chlorobenzene comprising adjusting the amount of chlorobenzene present, if necessary, so as to form a crystallisation liquor, cooling the crystallisation liquor to a crystallisation temperature so as to allow the bis-(4-chlorophenyl) sulphone to crystallise therefrom and separating the crystallised bis-(4-chlorophenyl) sulphone from the mother liquor, wherein the ratio of chlorobenzene to chlorobenzene sulphonic acid in the crystallisation liquor is such that the amount of crystallised bis-(4-chlorophenyl) sulphone is within 5 g, per 100 g of the reaction product, of the maximum amount of crystallised bis-(4-chlorophenyl) sulphone obtainable by adjustment of the amount of chlorobenzene present.

The ratio of chlorobenzene to chlorobenzene sulphonic acid of the reaction product may be adjusted to the required value by, for example, distilling off chlorobenzene if the ratio is too high or by adding chlorobenzene if it is too low. The reaction product however generally has a lower chlorobenzene content than that required for the present invention. Where chlorobenzene is added to the reaction product, it is preferably added at temperatures between 50° C and 150° C. If the reaction product has been allowed to cool below 50° C, some bis(4-chlorophenyl) sulphone will probably have crystallised already or the reaction product may be solid. In this situation, the reaction product is heated to 90° C to 115° C, so as to produce a homogeneous liquid and the chlorobenzene may be added before or after heating, to produce the crystallisation liquor.

It will be appreciated that in some cases it will not be necessary to adjust the chlorobenzene proportion as the reaction product may already have the solvents, i.e. chlorobenzene and chlorobenzene sulphonic acid, present in the necessary proportions. In that case the reaction product is used as the crystallisation liquor without change.

The crystallisation temperature is conveniently between 10° C and 30° C. Such a temperature is generally near ambient, and crystallisation at these temperatures reduces requirements for heated or cooled apparatus such as vessels, filters, centrifuges and pipework. It is preferred to carry out crystallisation at a temperature slightly below ambient (e.g. about 2° C below ambient).

For crystallisation temperatures of about 18° C and a typical reaction product containing about 8% chlorobenzene, 25% chlorobenzene sulphonic acid and 56% bis-(4-chlorophenyl) sulphone, and 11% bis(- chlorophenyl sulphone) isomers, the maximum amount of bis(4-chlorophenyl sulphone recoverable is 56-(0.746 × 25) parts, i.e. approximately 37 parts, per 100 parts of reaction product, requiring a chlorobenzene/chlorobenzene sulphonic acid ratio of about 0.74. This entails the addition of 10.5 parts of chlorobenzene to 100 parts of the reaction product. However the reaction product alone (chlorobenzene to chlorobenzene sulphonic acid ratio 0.32), or diluted with amounts of chlorobenzene so as to give ratios of chlorobenzene to chlorobenzene sulphonic acid of up to about 1.7, could be crystallised but with some unnecessary bis-(4-chlorophenyl) sulphone loss [undiluted gives about 36 parts per 100 parts of reaction product, while dilution to a ratio of 1.7, entailing the addition of 34.5 parts of chlorobenzene per 100 parts of reaction product, gives a recovery of 32 parts per 100 parts of reaction product, i.e. about 5 parts, per 100 parts of reaction product, less than the maximum recoverable.]

Preferred systems would use chlorobenzene/chlorobenzene sulphonic acid ratios of up to 1.35, but more preferably in the range 0.6 to 1.0. The use of too much added chlorobenzene not only reduces the amount of bis-(4-chlorophenyl) sulphone recovered but also adds to the problems of chlorobenzene recovery from the mother liquor.

To effect crystallisation, the crystallisation liquor is cooled, preferably slowly, to the crystallisation temperature (e.g. 10° C to 30° C, preferably about 2° C below ambient temperature), whereupon the desired bis-(4-chlorophenyl) sulphone crystallises from solution. Crystallisation is preferably commenced by seeding the liquor so as to reduce the risk of excessive supersaturation.

In one embodiment of the present invention, crystallisation liquor is fed to a crystallisation vessel containing a mixture of bis-(4-chlorophenyl) sulphone crystals and a saturated mother liquor of similar chlorobenzene to chlorobenzene sulphonic acid ratio to said crystallisation liquor at the crystallisation, e.g. ambient, temperature and further quantities of the desired sulphone allowed to crystallise.

Figure 4:
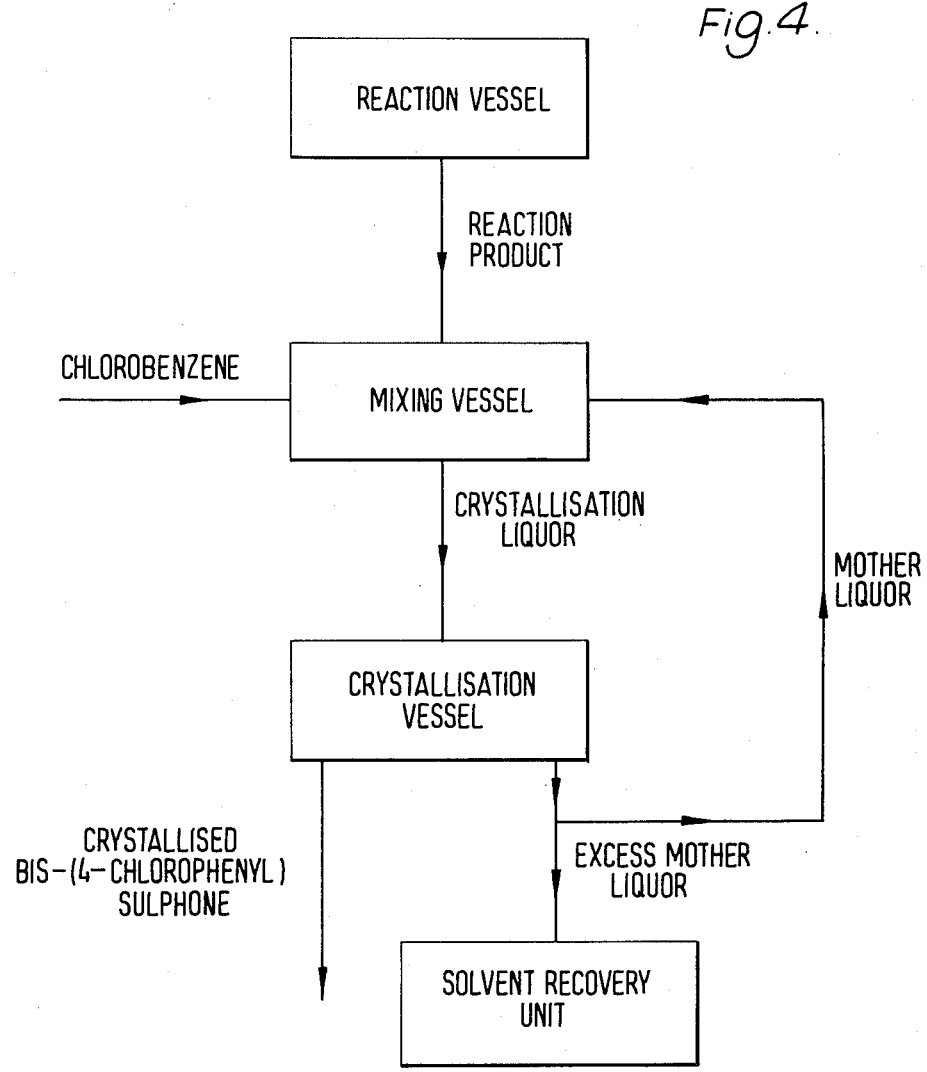

In a preferred system the ratio of chlorobenzene to chlorobenzene sulphonic acid of the reaction product is adjusted by adding chlorobenzene and mixing with the mother liquor obtained from previous crystallisations. This resulting crystallisation liquor is fed to the crystallisation vessel. Thus the mother liquor is recycled. A typical flow sheet is shown in FIG. 4.

Since chlorobenzene sulphonic acid is hygroscopic and hydrates readily to a hydrate having different solubility and melting characteristics, care should be taken to avoid the presence of moisture in the crystallisation process.

The vessels and pipework associated with the process of the invention must be fabricated from materials which do not contaminate the reaction product and crystallisation liquor. Stainless steel and glass-lined mild steel equipment is preferred.

The crystals may be collected by any conventional method such as filtration or centrifugation. The crystals so formed generally contain more than 96% by weight of bis-(4-chlorophenyl) sulphone, as generally the undesired bis-(chlorophenyl) sulphone isomers are not present in sufficient quantity to saturate the solution and hence crystallise. Typically the proportions of the bis-(chlorophenyl) sulphone isomers in the crystallisation liquor residuum, i.e. in the mother liquor obtained upon crystallisation of the bis(4-chlorophenyl) sulphone from the crystallisation liquor, will be as follows:

bis-4 isomer 50 – 90% by weight  
2,4' isomer 5 – 25% by weight  } based on weight of bis-(chlorophenyl) sulphone isomers  
3,4' isomer 5 – 25% by weight The chlorobenzene sulphonic acid in the mother liquor obtained upon crystallisation of the bis-(4-chlorophenyl) sulphone from the crystallisation liquor can be hydrolysed to sulphuric acid and chlorobenzene. The chlorobenzene in that mother liquor, i.e. that originally present and that resulting from hydrolysis can be recovered and used in further sulphone forming reactions. An additional advantage of the present invention is that only diluent already present in the reaction mixture is used and hence recovery of materials from the mother liquor obtained upon crystallisation of the bis-(4-chlorophenyl) sulphone from the crystallisation liquor is simplified.

The crystallised bis-(4-chlorophenyl) sulphone may be purified further by washing with, for example, small quantities of chlorobenzene (preferably cold) and/or by recrystallisation.

We have found that chlorobenzene, optionally mixed with 4-chlorobenzene sulphonic acid, is a particularly good solvent with which to effect recrystallisation.

Thus the impure bis-(4-chlorophenyl) sulphone may be recrystallised by dissolving the impure bis-(4-chlorophenyl) sulphone in a heated solvent comprising chlorobenzene and 0 to 60% by weight of 4-chlorobenzene sulphonic acid, based on the weight of the solvent, and thereafter cooling the solution to effect crystallisation of bis-(4-chlorophenyl) sulphone.

4-Chlorobenzene sulphonic acid is a good differential isomer solvent for the crystallisation of bis-(4-chlorophenyl) sulphone from its isomers, particularly the 2,4' and 3,4' isomers. However the 4,4' isomer is too soluble in cold 4-chlorobenzene sulphonic acid for the latter to be used economically as the sole recrystallisation solvent. The addition of chlorobenzene to 4-chlorobenzene sulphuric acid reduces the solubility of the 4,4' isomer at low temperature and such mixtures can be used economically. Chlorobenzene can be used as the sole recrystallisation solvent when the concentration of 2,4' and 3,4' isomers is relatively low.

The solvent used should not contain more than 60% by weight of 4-chlorobenzene sulphonic acid since then the 4,4' isomer will be too soluble for an economic process to be utilised. Preferably the solvent contains less than 50% by weight of 4-chlorobenzene sulphonic acid.

The concentrations of the hot recrystallisation solutions are determined by the solubility of the crude bis-(4-chlorophenyl) sulphone. When chlorobenzene is used by itself, the saturation concentration at the boiling point of chlorobenzene is about 90 g per 100 g of chlorobenzene. Naturally the concentration of the hot solution should not be so low that the solution will not be saturated when cold. At 18° C the solubility of bis-(4-chlorophenyl) sulphone in chlorobenzene alone is about 12 g per 100 g of chlorobenzene.

If desired the hot solution may be filtered prior to the recrystallisation.

The temperature at which the impure bis-(4-chlorophenyl) sulphone should be dissolved is preferably 40°–130° C while the recrystallisation temperature is preferably affected at −20° C to +30° C.

By this method bis-(4-chlorophenyl) sulphone in a purity of the order of 99% or more may be achieved.

The crystals may be dried by for example heating under partial vacuum at 50° C to 140° C.

The invention is illustrated by the following Examples.

EXAMPLE 1

In this Example the reaction product resulting from the reaction of chlorobenzene sulphonic acid and chlorobenzene had the following composition:
chlorobenzene — 7.7% by weight
chlorobenzene sulphonic acid — 25.3% by weight
bis-(4-chlorophenyl) sulphone — 56% by weight
2,4′ and 3,4′ bis-(chlorophenyl) sulphones — 10.5% by weight.

The ratio of chlorobenzene to chlorobenzene sulphonic acid was 0.304. The reaction product had a density of 1.322 g/ml at 100° C.

213 parts by weight of reaction product were heated to 110° C and 25 parts by weight of chlorobenzene were added to bring the chlorobenzene/chlorobenzene sulphonic acid ratio to about 0.77.

This solution was further diluted by addition to about 500 parts by weight of a liquor of density 1.32 g/ml at 18° C and having the following composition
chlorobenzene — 32.6% by weight
chlorobenzene sulphonic acid — 32.8% by weight
bis-(4-chlorophenyl) sulphone — 30.0% by weight
2,4′ and 3,4′ bis-(chlorophenyl) sulphones — 5.3% by weight This thus gave a crystallisation liquor of approximate composition
chlorobenzene — 27.6% by weight
chlorobenzene sulphonic acid — 29.4% by weight
bis-(4-chlorophenyl) sulphone — 36.3% by weight
2,4′ and 3,4′ bis-(chlorophenyl) sulphones — 6.7% by weight This crystallisation liquor had a chlorobenzene/chlorobenzene sulphonic acid ratio of 0.938. This crystallisation liquor was cooled slowly to 18° C with agitation whereupon the bis-(4-chlorophenyl) sulphone crystallised. The crystallised bis-(4-chlorophenyl) sulphone of purity >98.5% by weight was removed by filtration.

The yield of bis-(4-chlorophenyl) sulphone was 97.4 parts which is 95% of the theoretical amount obtainable from that crystallisation liquor at 18° C.

EXAMPLE 2

Crystallised bis-(4-chlorophenyl) sulphone obtained by a process similar to that described in Example 1 contained some chlorobenzene sulphonic acid and the 2,4′ and 3,4′ isomers as impurities.

In the impure material, 97.9% by weight of the bis(-chlorophenyl) sulphones was the desired 4,4′ isomer while the remaining 2.1% by weight was the unwanted 2,4′ and 3,4′ isomers. 100 parts by weight of the impure material was dissolved at 110° C in 100 parts by weight of chlorobenzene and cooled with stirring to 18° C when 82.71 parts by weight of crystals were formed and separated from the mother liquor. These crystals contained <0.2% by weight of 2,4′ isomer, 0.2% by weight of 3,4′ isomer, 0.76% by weight of chlorobenzene sulphonic acid and 98.84% by weight of 4,4′ isomer. When washed with hot water the 4-chlorobenzene sulphonic acid was removed to give bis-(4-chlorophenyl) sulphone of >99.5% by weight purity. Taking into account a solubility of bis-(4-chlorophenyl) sulphone in chlorobenzene at 18° C of 11.9% by weight and the original impurity level, the theoretical yield was 89.9 parts by weight and the yield 92% by weight of theoretical.

EXAMPLE 3

Bis-(4-chlorophenyl) sulphone (100 parts by weight) of purity 90% by weight contaminated mainly with the 3,4′ and 2,4° isomers obtained by a process similar to that described in Example 1 was dissolved in a mixture of chlorobenzene (83 parts by weight) and 4-chlorobenzene sulphonic acid (17 parts by weight) at 110° C. The hot solution was filtered and cooled slowly with stirring to 18° C. The crystalline material formed (73 parts by weight) was bis-(4-chlorophenyl) sulphone of 99.6% by weight purity.

We claim:

1. A process for the separation of bis-(4-chlorophenyl) sulphone from a crystallisation liquor comprising the reaction product obtained by reacting chlorobenzene sulphonic acid and chlorobenzene, comprising forming a crystallisation liquor, cooling the crystallisation liquor to a crystallisation temperature in the range 10° to 30° C so as to allow the bis-(4-chlorophenyl) sulphone to crystallise from the mother liquor, wherein the ratio of chlorobenzene to chlorobenzene sulphonic acid in the crystallisation liquor is such that the amount of crystallised bis-(4-chlorophenyl) sulphone is within 5 g, per 100 of the reaction product, of the maximum amount of crystallised bis-(4-chlorophenyl) sulphone obtainable at that crystallisation temperature by adjustment of the amount of chlorobenzene present.

2. A process according to claim 1 wherein the ratio of chlorobenzene to chlorobenzene sulphonic acid in the crystallisation liquor is less than 1.35.

3. A process according to claim 2 wherein the ratio of chlorobenzene to chlorobenzene sulphonic acid in the crystallisation liquor is in the range 0.6 to 1.0.

4. A process according to claim 1 in which chlorobenzene is added to the reaction product to obtain the crystallisation liquor.

5. A process according to claim 4 in which the chlorobenzene is added at temperatures between 50° C and 110° C.

6. A process according to claim 1 in which the chlorobenzene is removed from the reaction product to obtain the crystallisation liquor.

7. A process according to claim 1 in which the crystallisation liquor is fed to a crystallisation vessel containing a mixture of bis-(4-chlorophenyl) sulphone crystals and a saturated mother liquor, of similar chlorobenzene/chlorobenzene sulphonic acid ratio to said crystallisation liquor, at the crystallisation temperature and the bis-(4-chlorophenyl) sulphone is allowed to crystallise.

8. A process according to claim 1 in which the crystallised bis-(4-chlorophenyl) sulphone is recrystallised using a recrystallisation solvent comprising chlorobenzene and 0 to 60% by weight of the solvent of 4-chlorobenzene sulphonic acid.

* * * * *